United States Patent [19]
Gallant et al.

[11] Patent Number: 5,518,932
[45] Date of Patent: May 21, 1996

[54] CONTROL OF ETHYLENE ON ALKYL ALUMINUM CHAIN GROWTH PROCESSES USING CALORIMETRY

[75] Inventors: Robert P. Gallant, El Lago, Tex.; Isaac L. Smith, Baton Rouge, La.; Joseph B. Tedder, Jr., Seabrook, Tex.; Lloyd T. Crasto; George A. Daniels, both of Baton Rouge, La.

[73] Assignee: Albemarle Corporation, Richmond, Va.

[21] Appl. No.: 79,470

[22] Filed: Jun. 21, 1993

[51] Int. Cl.⁶ .................. G01N 33/20; G01N 25/20; C07C 1/00
[52] U.S. Cl. .................. 436/76; 436/81; 436/139; 436/147; 422/51; 585/328; 585/522
[58] Field of Search .................. 422/51; 436/76, 436/147, 81, 139; 585/328, 522

[56] References Cited

U.S. PATENT DOCUMENTS

| | | | |
|---|---|---|---|
| 3,160,477 | 1/1962 | Wasilewski | 23/253 |
| 3,716,333 | 2/1973 | Peuschel et al. | 23/230 R |
| 3,726,644 | 4/1973 | Desnoyers et al. | 23/230 R |
| 3,852,033 | 12/1974 | Hultman | 422/51 |
| 4,130,396 | 12/1978 | Böhm | 23/230 M |
| 4,152,117 | 5/1979 | Böhm | 23/230 R |
| 4,767,601 | 8/1988 | Kuerzinger et al. | 422/68 |
| 4,783,317 | 11/1988 | Kuerzinger et al. | 422/68 |
| 4,918,254 | 4/1990 | Diefenbach et al. | 585/328 |
| 4,935,569 | 6/1990 | Harkins et al. | 585/328 |
| 4,963,499 | 10/1990 | Stockton et al. | 436/147 |
| 5,049,687 | 9/1991 | Abazajian | 556/190 |

FOREIGN PATENT DOCUMENTS 1278500  6/1972  United Kingdom.

OTHER PUBLICATIONS

Determination of Alkylaluminum Compounds by Thermometric Titration, W. L. Everson et al., Analytical Chemistry, vol. 37, No. 7, Jun. 1965, pp. 806–811.
Enthalpimetric Analysis, Joseph Jordan, et al., Analytical Chemistry, vol. 48, No. 4, Apr. 1976, pp. 427A–439A.
Measurement of Total Organoaluminum–Reactable Impurities in Hydrocarbons by Continuous Flow Thermometric Analysis, T. R. Crompton, et al., Analytical Chemistry, vol. 40, No. 2, Feb. 1968, pp. 274–280.
Thermometric and Enthalpimetric Titrimetry, G. A. Vaughan, Van Nostraud Reinhold Co., 1973, pp. 3, 4, 16–19, 28, 29, 37–40, 96, 98, 175–177, 222, 227–230.

Primary Examiner—Robert J. Warden
Assistant Examiner—N. Bhat
Attorney, Agent, or Firm—David M. Bunnell

[57] ABSTRACT

The process of preparing higher aluminum alkyls by olefin chain growth on alkyl aluminum is improved by using on-line flow-through calorimetry to determine the aluminum concentration of a process stream, such as the aluminum alkyl feed stream, by reacting a sample portion of the process stream with a molar excess of alcohol and measuring the change in temperature. The aluminum concentration of the stream can then be adjusted as required to maintain it within a selected range.

9 Claims, 2 Drawing Sheets

CONTROL OF ETHYLENE ON ALKYL ALUMINUM CHAIN GROWTH PROCESSES USING CALORIMETRY

The invention relates generally to the control of alkyl aluminum concentrations in industrial processes and more specifically to the improved control of alkyl aluminum concentrations in α-olefin chain growth reactions by using continuous flow calorimetry.

The preparation of linear alpha-olefins having from about 4 to 20+ carbon atoms by the Ziegler chain growth process, which involves the reaction of an alkyl aluminum, such as triethylaluminum, with ethylene so as to add ethylene units to the alkyl groups and form a new trialkylaluminum product having a Poisson alkyl distribution, is a well known commercial process. The alpha-olefins are recovered and the alkyl aluminum is regenerated in a displacement reaction using, for example, ethylene or higher olefins to displace the alpha-olefins from the alkyl aluminum chain growth product.

The average number ($X_T$) of ethylene units added to each alkyl group is dependent in part on the concentration of triethylaluminum in the feed solution to the chain growth reaction. Because of commercial demand, olefins of certain carbon numbers are more valuable. Therefore, improved control of the chain growth reaction so as to consistently maximize the amount of the most valuable olefins produced in the process and to reduce the amount of carbon numbers where the supply exceeds the demand can provide a significant commercial benefit.

U.S. Pat. No. 4,152,117 discloses a process for periodically or continuously measuring very small concentrations, of less than 100 mmols/dm$^3$, of organoaluminum compounds, in their solutions which are used, for example, in the low pressure polymerization of α-olefins. The process measures the heat produced when the organoaluminum solution is reacted with a tertiary alcohol in a continuous flow apparatus.

We have now provided an improved process for preparing higher alkyl aluminum compounds by the chain growth reaction of a $C_2$ to $C_4$ olefin with an alkyl aluminum compound, wherein the alkyl aluminum concentration of one or more process streams is determined in order to monitor and control said process, the improvement comprising determining the alkyl aluminum concentration of at least one of said process streams by on-line, continuous flow calorimetry using a molar excess of an alcohol to hydrolyze a sample portion of said stream.

In one embodiment of the invention the alkyl aluminum concentration of the alkyl aluminum-olefin diluent feed solution to the chain growth reaction is determined calorimetrically by reacting a sample of the solution with an alcohol and the alkyl aluminum concentration of the feed solution is adjusted as necessary to provide the desired chain growth product distribution.

Also provided is an improved continuous ethylene chain growth process for producing α-olefins by the steps of (a) adding ethylene and a feed solution of alkyl aluminum in an olefin diluent, said solution having an aluminum concentration of from about 1.0 to 4.0 molar, to a reaction zone which is maintained under chain growth conditions so as to add one or more ethylene units to the alkyl groups of said alkyl aluminum and produce an alkyl aluminum chain growth product and thereafter, (b) reacting said growth product with an α-olefin so as to displace alkyl groups from said chain growth product and form free α-olefins corresponding to the displaced alkyl groups and alkyl aluminum which is returned to said feed solution, an improvement comprising, (i) determining the aluminum concentration of said feed solution by on-line, continuous flow calorimetry using a molar excess of an alcohol reactant to oxidize a sample portion of said free solution and (ii) adjusting the said concentration as necessary to maintain said concentration within a selected range.

Figure 1:
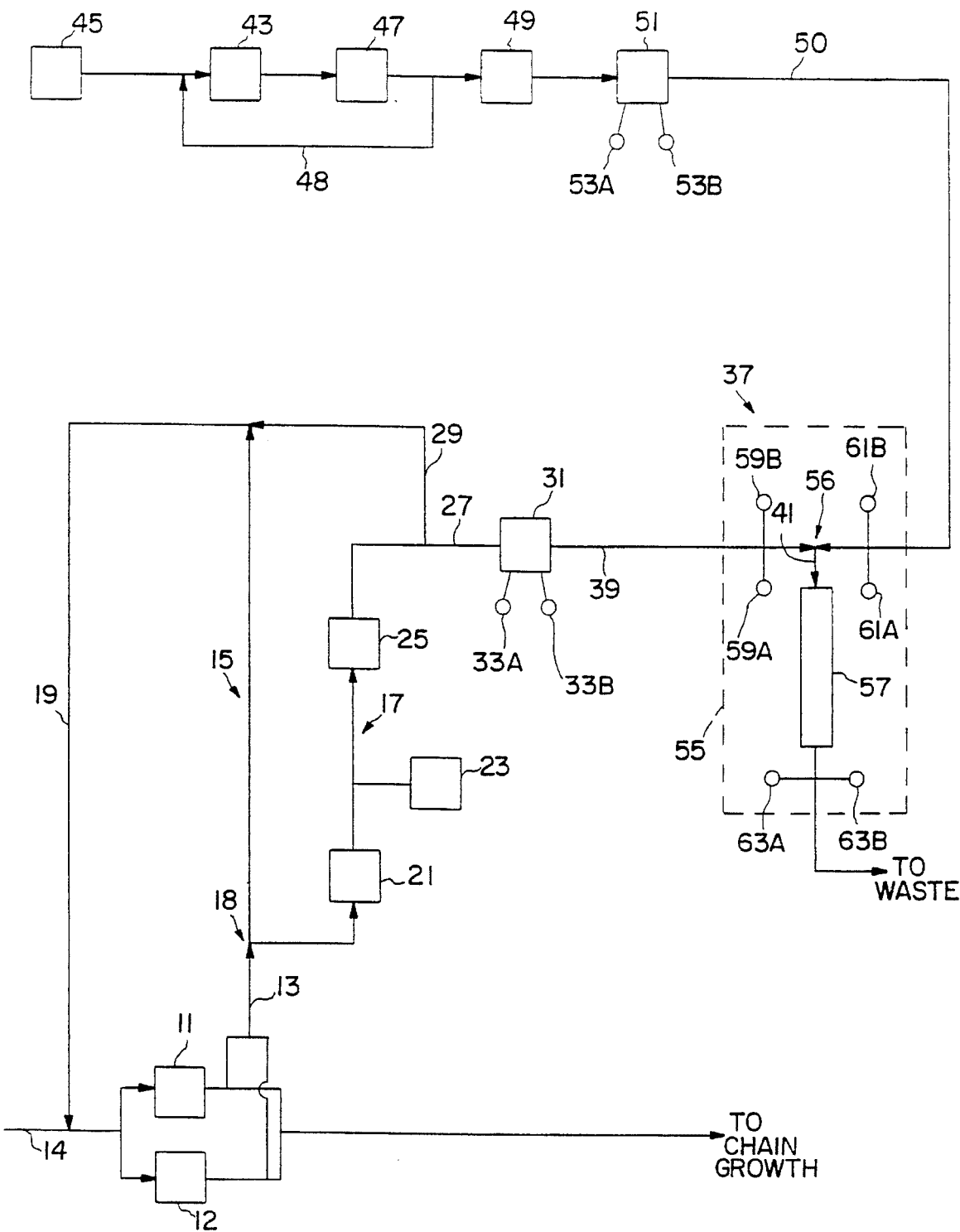
FIG. 1 is a schematic flow diagram illustrating an embodiment of the process using a continuous flow calorimeter for determining the alkylaluminum concentration of an olefin solution of the alkyl aluminum. Conventional equipment such as valves, and pressure and temperature indicators and the like have not been included in the drawing for the sake of clarity.

According to a typical chain growth process, a $C_2$ to $C_4$ olefin, e.g. ethylene, and an alkyl aluminum such as a trialkylaluminum, e.g. triethylaluminum, are fed to a chain growth reactor which is maintained under chain growth conditions. These conditions are a temperature in the range of about 90° C. to 260° C. and, preferably 120° C. to 175° C. and pressures in the range of about 2000 to 5000 psig and, preferably, 2500 to 3500 psig. The residence time of ethylene and TEA in the chain growth reaction is selected to be long enough to increase the chain length of the alkyls bonded to aluminum to an average chain length of about 6–12 carbon atoms ($X_T$=3 to 6). Depending on temperature and pressure, a residence time on the order of 15 minutes to about 1 hour is usually satisfactory.

A typical tubular chain growth reactor consists of two reactor shells operated in series. Each shell is a cylinder which contains a longitudinal coil of pipe having an inner diameter of 4". The coils are of sufficient length (about 3.5 miles) to provide the desired residence time. Boiler feed water is fed to the shell side of the reactor where it is vaporized by the heat liberated from the growth reaction taking place inside the tubes. A heat exchanger is used to recover the heat from the steam and the condensed water is returned to the reactor shell.

The chain growth product can be used, for example, to produce linear alcohols by oxidation and hydrolysis of the alkyl aluminum product or to produce linear α-olefins. To separate a linear α-olefin product, the chain growth product from the reactor is subjected to a series of flashes and one distillation column to remove excess ethylene and the olefin diluent ($C_{12}$). The product is then sent to a displacement reactor where the grown alkyl groups are displaced by ethylene to produce triethylaluminum and $C_4$ to about $C_{24}$ α-olefin products. After separation of the product α-olefins by distillation, the bottoms stream, which is a mixture of triethylaluminum which contains some tributyl and trihexyl species and residual olefins, is combined with a mixture of fresh and recycle ethylene to form the feed stream to the chain growth reactor.

Examples of patents which disclose variations of the ethylene chain growth process are
U.S. Pat. No. 2,863,896; U.S. Pat. No. 2,889,385;
U.S. Pat. No. 2,906,794; U.S. Pat. No. 2,971,969;
U.S. Pat. No. 3,180,881; U.S. Pat. No. 3,210,435;
U.S. Pat. No. 3,227,773; U.S. Pat. No. 3,278,633;
U.S. Pat. No. 3,352,940; U.S. Pat. No. 3,358,050;

U.S. Pat. No. 3,359,292; U.S. Pat. No. 3,384,651;
U.S. Pat. No. 3,391,291; U.S. Pat. No. 3,415,861;
U.S. Pat. No. 3,458,594; U.S. Pat. No. 3,487,097;
U.S. Pat. No. 3,663,647; U.S. Pat. No. 3,789,091;
U.S. Pat. No. 4,314,090; U.S. Pat. No. 4,918,254;
U.S. Pat. No. 4,935,569 and U.S. Pat. No. 5,049,687
whose teachings are incorporated herein by reference.

The distribution of olefin products from ethylene chain growth on triethylaluminum is a function of operating conditions in the chain growth reactors including the concentration of aluminum in the chain growth feed. The aluminum concentration of the alkyl aluminum feed is, for example, from about 1.0 to 4.0 molar and more commonly from about 2.0 to 3.0 molar (about 5.5 to 8.0 wt. % aluminum).

The process of the invention permits control of the ethylene chain growth reaction on the alkyl aluminum compound to provide a desired average $X_T$ of between about 3 to 6 by the steps of (a) determining the aluminum concentration of the alkyl aluminum in olefin diluent feed solution to the chain growth reaction by on-line, continuous flow calorimetry using an alcohol reactant to oxidize the alkyl aluminum in a sample portion of said feed solution and (b) adjusting the aluminum concentration based on the results of said determination to maintain said aluminum concentration within a selected range.

An aluminum analyzer is used in the process to provide both real time and continuous analysis. A real time analysis of aluminum concentration in the chain growth feed improves the ability to control at the selected distribution of grown alkyls, and increase the efficiency with which operating conditions can be changed to a new distribution of grown alkyls. The analyzer can also be operated on an intermittent basis.

Preferably, a Continuous Low Flow Calorimeter (CLFC) is employed which is an analytical device to determine the concentration of a reactive component based on the exothermic reaction with a reagent. The flow rate and temperature of the sample and reagent streams is accurately measured. The streams are mixed and the temperature change is accurately measured. The concentration of the reactive component is then calculated.

General Process Description

The CLFC aluminum analyzer calculates the aluminum concentration by measuring the temperature rise when a metered amount of chain growth feed is mixed with a metered amount of alcohol, which can be a mixture of alcohols. Non-limiting examples of suitable alcohols include straight or branched chain primary, secondary or tertiary alcohols having about 12 carbon atoms. The lower alcohols require higher pressure operation because the presence of vapor in the stream passing through the CLFC would cause calculation errors. Higher alcohols could be used but are not preferred because they may freeze at low ambient temperatures and their higher viscosity requires additional mixing time. Preferred alcohols are linear primary alcohols which contain about 6 to 12 carbon atoms such as octanol. Mixtures of alcohols can be used such as Ethyl EPAL® 810 alcohol which contains about 45 wt. % octanol 55 wt. % decanol. The primary alcohols will react with each of the alkyl groups in the aluminum alkyl. The flows of the aluminum and alcohol stream are adjusted to preferably provide a 1.5 to 10 times molar excess of alcohol. The temperature rise across the reactor is proportional to aluminum concentration. The triethylaluminum (TEA) in the chain growth feed, which typically contains about 20 to 30 wt. % TEA in a $C_2$ to $C_{14}$ olefin diluent reacts with the alcohol to form aluminum alkoxide, ethane and heat. The additional heat and ethane results in a higher bubble point pressure for the mixture. Vapor in the mixture would cause errors in the calculation, so that the CLFC reactor is run at pressures of from about 250 to 350 psig such as, for example 300 psig, to ensure a single phase mixture. Both feeds are flow controlled to avoid unnecessary changes to operating conditions. The streams are mixed in the CLFC reactor which is a short length of tube. Low flows are used, typically 2–15 cc/min. for the aluminum alkyl stream and 10–75 cc/min for the alcohol. Preferably, the flow rates and selected to use the minimum amounts of alcohol and alkyl aluminum at the necessary analysis precision, based on available low flow valves and meters. The alcohol flow rate is fixed by the desired temperature rise across the CLFC analyzer. There is no significant pressure drop through the CLFC reactor due to the low flow rates involved. The CLFC operating pressure is set above the bubble point of the CLFC reactor effluent. The pressure drop between the analyzer and the alkyl feed is set by the design of the alkyl flow control valve (typically 15 to 50 psi). The pressure drop between the analyzer and the alcohol supply is set by the design of the alcohol flow control valve (typically 50 to 100 psi).

The reactor tube is well insulated to eliminate heat losses to the environment. The calculation of the aluminum concentration uses the heat balance around the reactor. The inputs are the flow rate of alkyls and alcohol, the inlet temperature of the alkyls and alcohol and the outlet temperature of the mixture. The heat of reaction is a constant determined empirically. All temperature inputs to the calculation are the average readings of two sensors. All process equipment in the alkyl feed system is selected to minimize residence time. A typical residence time is estimated at 7.5 mins. The reason for using low flows is because this is a form of destructive testing, the alkyls and alcohol are consumed so that the operating costs are minimized by minimizing flows.

The sampling system and CLFC used in the following detailed process description of an embodiment of the invention is schematically illustrated in FIG. 1.

Detailed Process Description

Sample stream 13 of the aluminum alkyl-olefin chain growth feed material is taken at the chain growth feed booster pumps 11 and 12 located in the aluminum alkyl feed line 14. The sample stream goes to the analyzer through the 'speed loop' 15 at a rate of 50 gph at 150 psi and 110° F. A sample of the speed loop is taken at point 18 at the analyzer itself, this loop 17 has a flow rate of 200 cc/min. Loop 17 is included because the minimum pumping volume exceeds the flow to the analyzer. It also operates to control the residence time in the filters. The balance of the sample stream in the speed loop is returned to the process through line 19. Both loops are designed to minimize the time lag required to move the alkyl sample through the pipe.

The aluminum alkyl sample in loop 17 is filtered through a 30 micron filter and the pressure is boosted to 350 psi in pump 21. This pump is a duplex metering pump with a pulsation damper 23 installed down stream to minimize flow fluctuations. The sample stream is then fed to a 10 micron filter 25. Filtration of the sample stream is required to protect the flow meter 31. The selection of filter types is a compromise between overall sample residence time and the frequency with which filters are changed. The filtered aluminum alkyl sample is now piped as close as possible to the CLFC reactor 37 before the final sample of 3 cc/min is taken from loop 17 through line 27. The balance of the sample in loop 17 is returned to the process through lines 19 and 29.

The final aluminum alkyl sample to the CLFC reactor is metered by a positive displacement flow meter 31. The displacement meter is a volumetric flow device. The mass flow rate is calculated from the volumetric flow and the specific gravity (SG) of the liquid. The SG is calculated as a function of temperature using an average of the two RTD temperature sensors 33A and 33B located by the flow meter. The flow of aluminum alkyl is controlled at 3 cc/min by a flow control valve. The aluminum alkyl sample enters the CLFC reactor 37 through line 39 where it is mixed with alcohol from line 50 at mix point 56.

The alcohol feed system consists of a positive displacement alcohol pump 43 pressuring 115 cc/min up to 400 psig at ambient temperature to deliver EPAL 810 alcohol from supply 45. A pulsation damper 47 reduces flow fluctuations. The alcohol flow in line 50 to the analyzer is 15 cc/min, the balance is recycled back to the pump suction through line 48. The alcohol is filtered through a 10 micron filter 49, metered by a positive displacement flow meter 51, and the flow is controlled by a flow control valve. The volumetric flow is converted to mass flow using the SG that is correlated to fluid temperature using the average of two RTD sensors 53A and 53B located at the flow meter.

The CLFC reactor 37 is an insulated tubular reactor. It is housed in a 20" diameter PVC pipe filled with polyurethane foam insulation. The alkyl and alcohol feed tubes enter the PVC housing 55 and at the mix point 56. The mixture passes through a static mixer 57 to ensure complete mixing. The three tubes are arranged to keep 6" of insulation between each tube and the walls of the housing. The inlet RTDs for measuring the temperatures which are used in calculating the aluminum concentration are buried midway down the length of the housing to minimize the effects of heat conduction either from the mix point or from ambient conditions. The inlet aluminum stream alkyl temperature, alcohol inlet temperature, and mix temperature are all averages of two RTD sensors 59A & B, 61A & B and 63A & B, respectively. The RTDs are attached to the surface of the tubes using heat transfer epoxy glue.

Percent Aluminum Calculation

The process variables determined by the flow meter and sensors are transmitted to a process computer. The percent aluminum is calculated by the computer. The calculation proceeds in four steps. All of the process temperatures are redundant, therefore the first step is to calculate the average. The second step is to calculate the specific gravity of the process streams.

Average temperatures are used as input to the calculations. The third step calculates the mass flow rate of both alcohol and aluminum alkyl using the volumetric flow measurements transmitted from the field and the specific gravity calculated in step two. The final step is to calculate the wt. percent aluminum by the following equation:

$$\%Al = (Maa*Cpaa*(Tmx-Taa) + Mal*Cpal*(Tmx-Tal) + Hmx)*100 / (Hrxn*Maa)$$

%Al=Percent aluminum
Maa=Mass flow of aluminum alkyl stream
Cpaa=Heat capacity of aluminum alkyl stream
Tmx=Temperature of the effluent steam
Taa=Temperature of the aluminum alkyl stream
Mal=Mass flow of the alcohol stream
Cpal=Heat capacity of the alcohol stream
Tal=Temperature of the alcohol stream
Hmx=Heat of mixing
Hrxn=Heat of reactor Alternatively, the heat capacity terms can be made a function of stream temperature (or likewise control the temperature of the inlet streams). Other improvements of the equation would be to make the heat of reaction a function of temperature.

Figure 2:
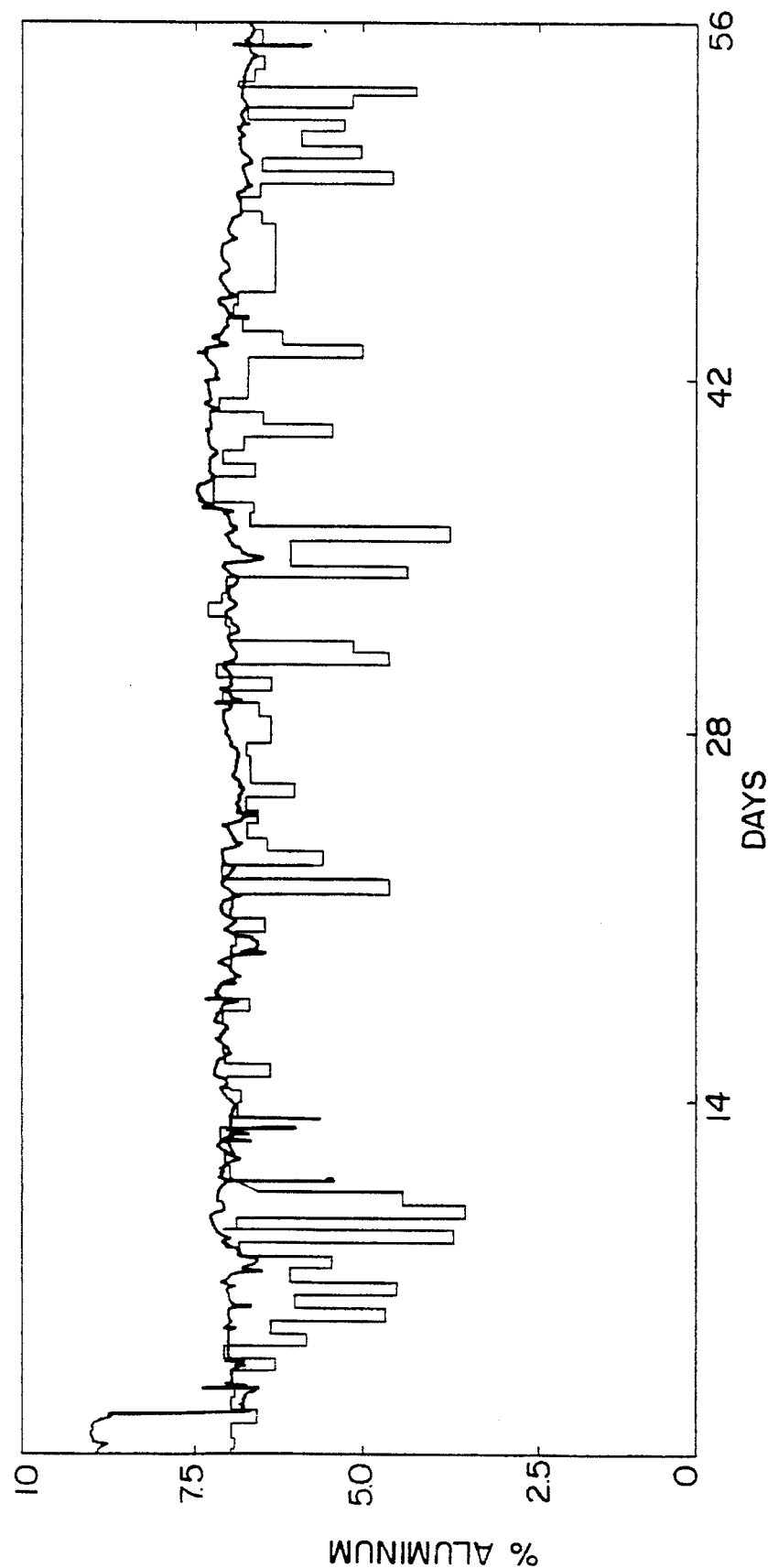
FIG. 2 is a trace showing an example of the triethylaluminum concentration analysis results obtained using a continuous flow calorimeter.

FIG. 2 is a trace showing a typical output of the analyzer for a 56 day period. A superimposed (square wave) from a corresponding off-line laboratory analyses is also shown which demonstrates a further advantage of the on line analysis in that the CLFC provided a more reliable analysis. The calculated percent aluminum value can be used to automatically adjust the aluminum concentration of the alkyl aluminum feed stream as part of a multivariable computer control scheme to provide a distribution of carbon numbers in the grown alkyls within selected values. The adjustment of the aluminum concentration can be accomplished, for example, by varying one or more of the following: (1) the amount of light olefin flashed from the chain growth feed; (2) the product olefin removal rate; (3) the flow rate of triethylaluminum makeup to the process; (4) the feed rate of the alkyl aluminum/olefin stream to chain growth; or (5) the chain growth $X_T$.

Continuous Low Flow Calorimeters can be used to analyze other aluminum alkyl containing streams which are present in the manufacture of α-olefins. For example the aluminum content of the chain growth product stream from which the $X_T$ can be inferred. For most streams, it is not necessary to boost the pressure and pump 21 can be omitted. The CLFC can also be adapted to determine the alkyl aluminum concentration in other processes such as (a) aluminum alkyl manufacture, (b) linear alcohol manufacture from aluminum alkyl compounds, (c) aluminum hydride manufacture, (d) magnesium alkyl manufacture, (e) aluminoxane manufacture from alkyl aluminum compounds, etc. For some aluminum alkyl containing streams, such as those present in aluminum alkyl manufacture, a third stream of inert diluent (e.g. a hydrocarbon solvent) could be included because of the high energy released in the hydrolysis section.

What is claimed is:

1. An improved process for preparing higher alkyl aluminum compounds by the chain growth reaction of a $C_2$ to $C_4$ olefin with an alkyl aluminum compound, wherein the alkyl aluminum concentration of one or more process streams is determined in order to monitor and control said process, the improvement comprising determining the alkyl aluminum concentration of at least one of said process streams by on-line, continuous flow calorimetry using a molar excess of a primary alcohol to hydrolyze a sample portion of said stream by reacting with each of the alkyl groups in said alkyl aluminum compound.

2. The process of claim 1 wherein said alkyl aluminum concentration is from about 1.0 to 4.0 molar and from about a 1.5 to 10 times molar excess of said primary alcohol is used.

3. The process of claim 2 wherein said primary alcohol comprises one or more linear primary alcohols having from about 6 to 12 carbon atoms.

4. The process of claim 3 wherein said alkyl aluminum compound is triethylaluminum.

5. In a continuous ethylene chain growth process for producing α-olefins comprising the steps of (a) adding ethylene and a feed solution of alkyl aluminum in an olefin diluent, said solution having an aluminum concentration of from about 1.0 to 4.0 molar, to a reaction zone which is maintained under chain growth conditions so as to add one or more ethylene units to the alkyl groups of said alkyl aluminum and produce an alkylaluminum chain growth product, and thereafter (b) reacting said chain growth product with an α-olefin so as to displace alkyl groups from said chain growth product and form free α-olefin corresponding to the displaced alkyl groups and alkyl aluminum which is returned with said feed solution to said reaction zone, the improvement comprising (i) determining the aluminum concentration of said feed solution by on-line, continuous flow calorimetry using a molar excess of a primary alcohol reactant to oxidize a sample portion of said solution by reacting with each of the alkyl groups in said alkyl aluminum and (ii) adjusting said aluminum concentration as necessary to maintain said aluminum concentration within a selected range.

6. The process of claim 5 wherein the aluminum concentration in a trialkyl aluminum containing feed solution is determined by (a) continuously or intermittently removing said sample portion from said feed solution, (b) mixing said sample portion with from about a 1.5 to 10 times molar excess of said primary alcohol in a continuous flow calorimeter, (c) measuring the change in temperature caused by the reaction of the trialkyl aluminum in said sample portion with said primary alcohol, and (d) using a process control computer to calculate the aluminum concentration in said sample portion of said feed solution from said change in temperature.

7. The process of claim 6 wherein said process control computer is used to maintain said aluminum concentration within said selected range.

8. The process of claim 6 wherein said primary alcohol comprises one or more linear, primary alcohols having from about 6 to 12 carbon atoms and said trialkyl aluminum is triethyl aluminum.

9. The process of claim 6 wherein the pressure of said sample portion is increased prior to mixing it with said primary alcohol such that a single phase mixture is maintained in the calorimeter.

\* \* \* \* \*